United States Patent [19]

Findeisen et al.

[11] Patent Number: 5,332,719
[45] Date of Patent: Jul. 26, 1994

[54] SUBSTITUTED TRIAZOLINONES

[75] Inventors: Kurt Findeisen; Dietmar Kuhnt, both of Leverkusen; Klaus-Helmut Müller, Duesseldorf; Klaus König, Odenthal; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 539

[22] Filed: Jan. 4, 1993

Related U.S. Application Data

[63] Continuation of Ser. No. 847,139, Mar. 6, 1992, abandoned.

[30] Foreign Application Priority Data

Mar. 14, 1991 [DE] Fed. Rep. of Germany ....... 4108187

[51] Int. Cl.$^5$ .................. A01N 43/653; C07D 249/12
[52] U.S. Cl. .................................. 504/273; 548/263.8
[58] Field of Search ...................... 548/263.8; 504/273

[56] References Cited

U.S. PATENT DOCUMENTS 5,061,311 10/1991 Findeisen et al. ...................... 71/92
5,194,084 3/1993 Findeisen et al. ................. 548/263.8

FOREIGN PATENT DOCUMENTS 398096 11/1990 European Pat. Off. ......... 548/263.8

*Primary Examiner*—Patricia L. Morris
*Attorney, Agent, or Firm*—Sprung Horn Kramer & Woods

[57] ABSTRACT

The invention relates to new substituted triazolinones of the formula (I)

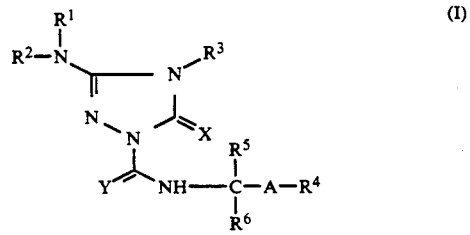

in which
A represents a radical of the formula

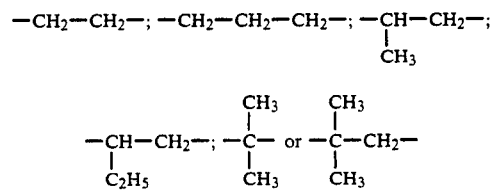

X and Y each represent O or S and the radicals $R^1$–$R^6$ have the meanings mentioned in the description, processes for their preparation and their use as herbicides.

4 Claims, No Drawings

SUBSTITUTED TRIAZOLINONES

This application is a continuation of application Ser. No. 847,139, filed Mar. 6, 1992 now abandoned.

The invention relates to new substituted triazolinones, processes for their preparation and their use as herbicides.

It has been disclosed that certain substituted triazolinones such as, for example, the compound 1-(4-phenyl-2-butyl-minocarbonyl) -3-dimethylamino-4-methyl-1,2, 4-triazolin-5-one have herbicidal properties ( compare, for example, DE-OS ( German Published Specification ) 3,709,574).

However, the herbicidal activity of these previously known compounds against problem weeds, like their tolerability towards important crop plants, is not completely satisfactory in all areas of application.

New substituted triazolinones have now been found of the general formula (I)

$$\begin{array}{c} R^1 \\ | \\ R^2-N \diagdown \diagup N-R^3 \\ N \diagdown N \diagup \diagdown X \\ | \quad \quad R^5 \\ Y \quad NH-C-A-R^4 \\ \quad \quad \quad | \\ \quad \quad \quad R^6 \end{array} \quad (I)$$

in which
A represents a radical of the formula $-CH_2-CH_2-$; $-CH_2-CH_2-CH_2-$; $-CH-CH_2-$;
$\qquad\qquad\qquad\qquad\qquad\qquad\qquad | $
$\qquad\qquad\qquad\qquad\qquad\qquad\qquad CH_3$ $\qquad\qquad\qquad\qquad\qquad CH_3 \qquad CH_3$
$\qquad\qquad\qquad\qquad\qquad\quad | \qquad\qquad | $
$-CH-CH_2-$; $-C-$ or $-C-CH_2-$
$\quad | \qquad\qquad\quad | \qquad\qquad | $
$\quad C_2H_5 \qquad\quad CH_3 \qquad\quad CH_3$ X represents oxygen or sulphur,
Y represents oxygen or sulphur,
$R^1$ represents hydrogen or alkyl,
$R^2$ represents alkyl,
$R^3$ represents alkyl or alkenyl,
$R^4$ represents cycloalkyl or aryl which is in each case optionally substituted,
$R^5$ represents alkyl or alternatively represents hydrogen in the case in which not, simultaneously, A represents $-CH_2-CH_2-$ and $R^4$ represents unsubstituted phenyl and
$R^6$ represents alkyl or cyano or alternatively represents hydrogen in the case in which A simultaneously represents a branched alkanediyl radical of the formula $\qquad\qquad\qquad\qquad\qquad\qquad CH_3 \qquad CH_3$
$\qquad\qquad\qquad\qquad\qquad\qquad\quad | \qquad\qquad | $
$-CH-CH_2-$; $-CH-CH_2-$; $-C-$ or $-C-CH_2-$
$\quad | \qquad\qquad\quad | \qquad\qquad\qquad | \qquad\qquad | $
$\quad CH_3 \qquad\quad C_2H_5 \qquad\quad CH_3 \qquad\quad CH_3$ or
$R^5$ and $R^6$ together represent a doubly linked alkanediyl radical.

Furthermore, it has been found that the new substituted triazolinones of the general formula (I)

$$\begin{array}{c} R^1 \\ | \\ R^2-N \diagdown \diagup N-R^3 \\ N \diagdown N \diagup \diagdown X \\ | \quad \quad R^5 \\ Y \quad NH-C-A-R^4 \\ \quad \quad \quad | \\ \quad \quad \quad R^6 \end{array} \quad (I)$$

in which
A represents a radical of the formula $-CH_2-CH_2-$; $-CH_2-CH_2-CH_2-$; $-CH-CH_2-$;
$\qquad\qquad\qquad\qquad\qquad\qquad\qquad | $
$\qquad\qquad\qquad\qquad\qquad\qquad\qquad CH_3$ $\qquad\qquad\qquad\qquad\qquad CH_3 \qquad CH_3$
$\qquad\qquad\qquad\qquad\qquad\quad | \qquad\qquad | $
$-CH-CH_2-$; $-C-$ or $-C-CH_2-$
$\quad | \qquad\qquad\quad | \qquad\qquad | $
$\quad C_2H_5 \qquad\quad CH_3 \qquad\quad CH_3$ X represents oxygen or sulphur,
Y represents oxygen or sulphur,
$R^1$ represents hydrogen or alkyl,
$R^2$ represents alkyl,
$R^3$ represents alkyl or alkenyl,
$R^4$ represents cycloalkyl or aryl which is in each case optionally substituted,
$R^5$ represents alkyl or alternatively represents hydrogen in the case in which, not simultaneously, A represents $-CH_2-CH_2-$ and $R^4$ represents unsubstituted phenyl and
$R^6$ represents alkyl or cyano or alternatively represents hydrogen in the case in which A simultaneously represents a branched alkanediyl radical of the formula $\qquad\qquad\qquad\qquad\qquad\qquad CH_3 \qquad CH_3$
$\qquad\qquad\qquad\qquad\qquad\qquad\quad | \qquad\qquad | $
$-CH-CH_2-$; $-CH-CH_2-$; $-C-$ or $-C-CH_2-$
$\quad | \qquad\qquad\quad | \qquad\qquad\qquad | \qquad\qquad | $
$\quad CH_3 \qquad\quad C_2H_5 \qquad\quad CH_3 \qquad\quad CH_3$ or
$R^5$ and $R^6$ together represent a doubly linked alkanediyl radical,
are obtained when
a) 1-chloro-(thio)-carbonyltriazolinones of the formula (II)

$$\begin{array}{c} R^1 \\ | \\ R^2-N \diagdown \diagup N-R^3 \\ N \diagdown N \diagup \diagdown X \\ | \\ Y \diagdown Cl \end{array} \quad (II)$$

in which $R^1$, $R^2$, $R^3$, X and Y have the abovementioned meaning, are reacted with amines of the formula (III)

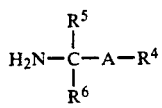

in which $R^4$, $R^5$, $R^6$ and A have the abovementioned meaning, if appropriate in the presence of a diluent and if appropriate in the presence of a reaction auxiliary, or when b) triazolinones unsubstituted in the 1-position, of the formula (IV)

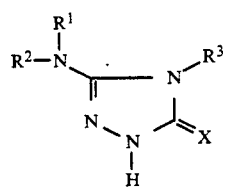

in which $R^1$, $R^2$, $R^3$ and X have the abovementioned meaning, are reacted with iso-(thio)-cyanates of the formula (V)

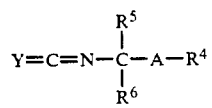

in which A, Y, $R^4$, $R^5$ and $R^6$ have the abovementioned meaning, if appropriate in the presence of a diluent and if appropriate in the presence of a reaction auxiliary.

Finally, it has been found that the new substituted triazolinones of the general formula (I) have herbicidal properties.

Surprisingly, the substituted triazolinones of the formula (I) according to the invention exhibit a considerably better herbicidal activity against problem weeds and simultaneously a comparatively good tolerability towards important crop plants in comparison with the substituted triazolinones known from the prior art, such as, for example, the compound 1-(4-phenyl-2-butylaminocarbonyl)-3-dimethylamino-4-methyl-1,2,4-triazolin-5-one, which, chemically and with respect to their action, are obvious compounds.

Formula (I) provides a general definition of the substituted triazolinones according to the invention. Preferred compounds of the formula (I) are those in which A represents a radical of the formula

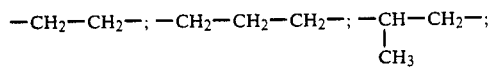

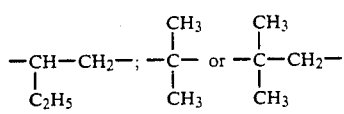

X represents oxygen or sulphur,
Y represents oxygen or sulphur,
$R^1$ represents hydrogen or straight-chain or branched alkyl having 1 to 6 carbon atoms,
$R^1$ represents straight-chain or branched alkyl having 1 to 6 carbon atoms, $R^3$ represents straight-chain or branched alkyl having 1 to 6 carbon atoms or represents straight-chain or branched alkenyl having 2 to 6 carbon atoms, $R^4$ represents cycloalkyl having 3 to 7 carbon atoms which is optionally monosubstituted or polysubstituted by identical or different substituents, suitable substituents being: straight-chain or branched alkyl having 1 to 4 carbon atoms, or represents phenyl or naphthyl which is in each case optionally monosubstituted or polysubstituted by identical or different substituents, suitable substituents being: halogen, cyano, nitro, in each case straight-chain or branched alkyl, alkoxy or alkylthio each having 1 to 4 carbon atoms, in each case straight-chain or branched halogenoalkyl, halogenoalkoxy or halogenoalkylthio each having 1 to 4 carbon atoms; in each case straight-chain or branched alkoxycarbonyl or alkoximinoalkyl each having 1 to 4 carbon atoms in the individual alkyl moieties; dialkylamino in each case having 1 to 4 carbon atoms; in the individual straight-chain or branched alkyl moieties, N-alkanoylamino having 1 to 5 carbon atoms in the straight-chain or branched alkanoyl moiety, doubly linked dioxyalkylene having 1 to 3 carbon atoms which is optionally monosubstituted or polysubstituted by identical or different halogen substituents and phenyl which is optionally monosubstituted or polysubstituted by identical or different halogen substituents and/or straight-chain or branched alkyl having 1 to 4 carbon atoms, $R^5$ represents straight-chain or branched alkyl having 1 to 6 carbon atoms or alternatively represents hydrogen in the case in which not, simultaneously, A represents $-CH_2-CH_2-$ and $R^4$ represents unsubstituted phenyl and $R^6$ represents cyano or represents straight-chain or branched alkyl having 1 to 6 carbon atoms or alternatively represents hydrogen in the case in which A simultaneously represents a branched alkanediyl radical of the formula

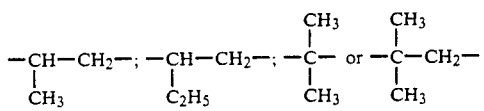

or
$R^5$ and $R^6$ together represent a doubly linked alkanediyl radical having 2 to 7 carbon atoms.

Particularly preferred compounds of the formula (I) are those in which

A represents a radical of the formula

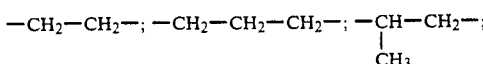

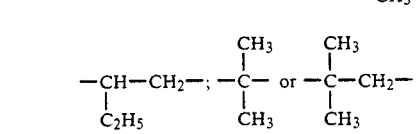

X represents oxygen or sulphur,
Y represents oxygen or sulphur,
$R^1$ represents hydrogen or straight-chain or branched alkyl having 1 to 4 carbon atoms, $R^2$ represents straight-chain or branched alkyl having 1 to 4 carbon atoms, $R^3$ represents straight-chain or branched alkyl having 1 to 4 carbon atoms or straight-chain or branched alkenyl having 2 to 5 carbon atoms, $R^4$ represents cyclohexyl which is optionally monosubstituted to trisubstituted by identical or different substituents, suitable substituents being: methyl, ethyl or isopropyl or represents phenyl or naphthyl which is in each case optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, difluoromethyl, trifluoromethoxy, trifluoromethylthio, methoxycarbonyl, ethoxycarbonyl, propoxycarbonyl, dimethylamino, N-acetamido, methoximinomethyl, methoximinoethyl, ethoximinomethyl, ethoximinoethyl, dioxymethylene, difluorodioxymethylene, tetrafluorodioxyethylene or phenyl which is optionally monosubstituted to trisubstituted by identical or different fluorine, chlorine, bromine, methyl and/or ethyl substituents, $R^5$ represents straight-chain or branched alkyl having 1 to 4 carbon atoms or alternatively represents hydrogen in the case in which, A not simultaneously, represents —CH$_2$—CH$_2$— and $R^4$ represents unsubstituted phenyl and $R^6$ represents cyano or represents straight-chain or branched alkyl having 1 to 4 carbon atoms or alternatively represents hydrogen in the case in which A simultaneously represents a branched alkanediyl radical of the formula $$-CH-CH_2-;\ -CH-CH_2-;\ -C-\ \text{or}\ -C-CH_2-$$
$$\begin{array}{cccc} | & | & | & | \\ CH_3 & C_2H_5 & CH_3 & CH_3 \end{array}$$
with CH$_3$ substituents above C positions or $R^5$ and $R^6$ together represent a doubly linked alkanediyl radical having 4 to 5 carbon atoms.

Very particularly preferred compounds of the formula (I) are those in which

A represents a radical of the formula $$-CH_2-CH_2-;\ -CH_2-CH_2-CH_2-;\ -CH-CH_2-;$$
$$\qquad\qquad\qquad\qquad\qquad\qquad\qquad\quad |$$
$$\qquad\qquad\qquad\qquad\qquad\qquad\qquad\ CH_3$$

$$-CH-CH_2-;\ -C-\ \text{or}\ -C-CH_2-$$

X represents oxygen,
Y represents oxygen,
$R^1$ represents hydrogen or methyl,
$R^2$ represents methyl,
$R^3$ represents methyl, ethyl, n-or i-propyl, n-, i-, s- or t-butyl or vinyl, allyl, n- or i-butenyl,
$R^4$ represents cyclohexyl which optionally monosubstituted to trisubstituted by methyl and/or ethyl, or represents phenyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, difluoromethyl, trifluoromethoxy, trifluoromethylthio, methoxycarbonyl, ethoxycarbonyl, propoxycarbonyl, dimethylamino, N-acetamido, dioxymethylene, difluorodioxymethylene, tetrafluorodioxyethylene or phenyl which is optionally monosubstituted to trisubstituted by identical or different fluorine, chlorine, bromine, methyl and/or ethyl substituents, $R^5$ represents straight-chain or branched alkyl having 1 to 4 carbon atoms or alternatively represents hydrogen in the case in which not, simultaneously, A represents —CH$_2$—CH$_2$— and $R^4$ represents unsubstituted phenyl and $R^6$ represents cyano or represents straight-chain or branched alkyl having 1 to 6 carbon atoms or alternatively represents hydrogen in the case in which A simultaneously represents a branched alkanediyl radical of the formula $$-CH-CH_2-;\ -CH-CH_2-;\ -C-\ \text{or}\ -C-CH_2-$$

or $R^5$ and $R^6$ together represent a doubly linked pentanediyl radical.

The abovementioned definitions or illustrations of radicals, mentioned generally or in preference ranges, can be combined with one another in any desired manner, i.e. also between the particular preference ranges.

If, for example, 1-chlorocarbonyl-3-dimethylamino-4-methyl-1,2,4-triazolin-5-one and 1-( 4-methylphenyl )-3-aminobutane are used as starting substances, the course of the reaction of process (a) according to the invention can be represented by the following equation:

[Reaction scheme showing 3-dimethylamino-4-methyl-1,2,4-triazolin-5-one with chlorocarbonyl group reacting with H$_2$N—CH(CH$_3$)—CH$_2$—CH$_2$—C$_6$H$_4$—CH$_3$ with −HCl/Base to give the coupled product NH—CH(CH$_3$)—CH$_2$—CH$_2$—C$_6$H$_4$—CH$_3$]

If, for example, 3-dimethylamino-4-methyl-1,2,4-triazolin-5-one and 3-methyl-4-phenyl-2-butylisocyanate are used as starting substances, the course of the reaction of process (b) according to the invention can be represented by the following equation:

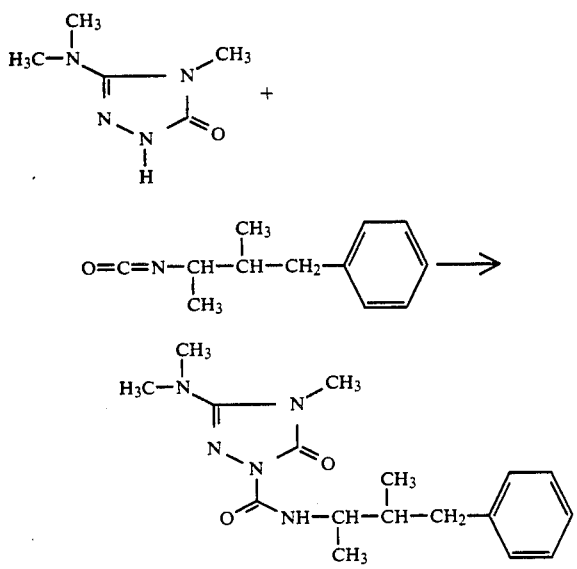

Formula (II) provides a general definition of the 1-chloro-(thio)-carbonyltriazolinones needed as starting substances for carrying out process (a) according to the invention. In this formula (II), $R^1$, $R^2$, $R^3$, X and Y preferably represent those radicals which have already been mentioned as preferred for these substituents in connection with the description of the compounds of the formula (I) according to the invention.

The 1-chloro-( thio )-carbonyltriazolinones of the formula (II) are known or can be obtained in analogy to known processes (compare, for example, EP 283,876).

Formula (III) provides a general definition of the a mines furthermore needed as starting substances for carrying out process (a) according to the invention. In this formula (III), $R^4$, $R^5$, $R^6$ and A preferably represent those radicals which have already been mentioned as preferred for these substituents in connection with the description of the compounds of the formula (I) according to the invention.

The amines of the formula (III) are known or can be obtained in analogy to known processes (compare, for example, Coll. Czech. Chem. Commun. 35, 2810–2830 [1970]; Synth. Commun. 18, 29–35 [1988]; Angew. Chem. 96, 368–369 [1984]; DE-OS (German Published Specification) 2,825,961; DE-OS (German Published Specification) 3,222,152; U.S. Pat. No. 4,906,645; EP 320,898; U.S. Pat. No. 4,695,589; EP 237,305, U.S. Pat. No. 4,374,149; EP 28,105; EP 6,614; Nouv. J. Chim. 1, 243–254 [1977] and CA 87: 151614a).

Formula (IV) provides a general definition of the triazolinones unsubstituted in the 1-position needed as starting substances for carrying out process (b) according to the invention. In this formula (IV), $R^1$, $R^2$, $R^3$ and X preferably represent those radicals which have already been mentioned as preferred for these substituents in connection with the description of the compounds of the formula ( I ) according to the invention.

The triazolinones unsubstituted in the 1-position of the formula (IV) are known or can be obtained in analogy to known processes (compare, for example, EP 283,876).

Formula (V) provides a general definition of the iso-(thio)-cyanates needed as starting substances for carrying out process (b) according to the invention. In this formula (V), $R^4$, $R^5$, $R^6$, A and Y preferably represent those radicals which have already been mentioned as preferred for these substituents in connection with the description of the compounds of the formula (I) according to the invention.

The iso-(thio)-cyanates of the formula (V) are known in some cases ( compare, for example, Nouv. J. Chim. 1, 243–254 [1977] and CA 87: 151614a; U.S. Pat. No. 4,035,404) or can be obtained in analogy to known processes (compare, for example, Synthesis 1977, 756; Org. Syntheses Coll. Vol. IV, 521 [1963] or "Organikum" VEB Deutscher Verlag der Wissenschaften Berlin 1981, p. 703), for example by reacting amines of the formula (III)

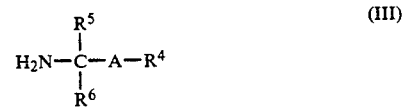

in which $R^4$, $R^5$, $R^6$ and A have the abovementioned meaning, with phosgene or thiophosgene, if appropriate in the presence of a diluent such as, for example, toluene or chlorobenzene, at temperatures between $-10°$ C. and $+150°$ C.

Suitable diluents for carrying out process (a) according to the invention are inert organic solvents. These include in particular aliphatic, allcyclic or aromatic, optionally halogenated hydrocarbons, such as, for example, benzinc, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate or bases such as pyridine.

Process (a) according to the invention can optionally be carried out in the presence of a suitable acid-binding agent as a reaction auxiliary. Those which are suitable are all customary inorganic or organic bases. These include, for example, alkaline earth metal or alkali metal hydroxides, such as sodium hydroxide, calcium hydroxide, potassium hydroxide or alternatively ammonium hydroxide, alkali metal carbonates, such as sodium carbonate, potassium carbonate, potassium hydrogen carbonate, sodium hydrogen carbonate, or ammonium carbonate, alkali metal or alkaline earth metal acetates, such as sodium acetate, potassium acetate, calcium acetate or ammoniumacetate, and tertiary a mines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

It is also possible to employ the amine of the formula (III) used as the reaction components in an appropriate excess simultaneously as the acid-binding agent.

The reaction temperatures can be varied within a substantial range when carrying out process (a) according to the invention. In general, the reaction is carried out at temperatures between 0° C. and +150° C., preferably at temperatures between +10° C. and +80° C.

To carry out process (a) according to the invention, 1.0 to 5.0 mol, preferably 1.0 to 2.5 mol, of amine of the formula (III) and optionally 1.0 to 5.0 mol, preferably 1.0 to 2.5 mol, of base used as the reaction auxiliary are in general employed per mole of 1-chloro-(thio)-carbonyltriazolinone of the formula (II).

The reaction is carried out, and the reaction products are worked up and isolated according to known processes (for this purpose compare, for example, EP 283,876 or the Preparation Examples).

Suitable diluents for carrying out process (b) according to the invention are likewise inert organic solvents. Preferably, the solvents mentioned in the case of process (a) are used.

Process (b) according to the invention is preferably carried out in the presence of a suitable basic reaction auxiliary. Those suitable are all customary inorganic or organic bases. Tertiary amines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU) are preferably used. However, the addition of basic reaction auxiliaries of this type is not absolutely necessary.

The reaction temperatures can be varied within a substantial range when carrying out process (b) according to the invention. In general, the reaction is carried out at temperatures between 0° C. and +150° C., preferably at temperatures between +40° C. and +120° C.

Process (b) according to the invention is customarily carried out under normal pressure. However, it is also possible, in particular in the case of gaseous starting compounds, to work at elevated pressure.

To carry out process (b) according to the invention, 1.0 to 5.0 mol, preferably 1.0 to 2.5 mol, of iso-(thio)-cyanate of the formula (V) and optionally 1.0 to 5.0 mol, preferably 1.0 to 2.5 mol, of base used as the reaction auxiliary are in general employed per mole of triazolinone unsubstituted in the 1-position of the formula (IV).

The reaction is carried out, and the reaction products are worked up and isolated according to known processes (for this purpose compare, for example, EP 283,876 or the Preparation Examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonurn, Sesbania, Ambrosia, Cirsium, Carduus, Sonchus, Solanum, Rorippa, Rotala, Lindernia, Lainlure, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants. The compounds are suitable, depending on the concentration, for the total combating of weeds, for example on industrial terrain and rail tracks, and on paths and squares with or without tree plantings. Equally, the compounds can be employed for combating weeds in perennial cultures, for example forestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land and for the selective combating of weeds in annual cultures.

The active compounds according to the invention can be employed to particularly good effect here for combating mono- and dicotyledon weeds, in particular in monocotyledon cultures such as, for example, wheat.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foe-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one METAMITRON) for combating weeds in sugar beet, and 4-amino-6(1,1-dimethylethyl)-3-methylthio-1,2,4-triazin-5(4 H)-one (METRIBUZIN) for combating weeds in soya beans. Mixtures with 2,4-dichlorophenoxyacetic acid (2,4-D); 4-(2,4-dichlorophenoxy)-butyric acid (2,4-DB; 2,4-di-chloro-phenoxypropionic acid (2,4-DP); (2-methyl-4-chlorophenoxy)-acetic acid (MCPA); 4-(4-chloro-2-methyl)-phenoxybutyric acid (MCPB); [(4-amino-3,5-dichloro-6-fluoro-2-pyridinyl)-oxy]-acetic acid or its 1-methylheptyl ester (FLUROXYPYR); 2-[4-(2,4-dichlorophenoxy)phenoxy]-propionic acid, its methyl or its ethyl ester (DICLOFOP); 2-{4-[(6-chloro-2-benzoxazolyl)-oxy]phenoxy}-propanoic acid, its methyl or ethyl ester (FENOXAPROP); N-(1-ethylpropyl)-3,4-dimethyl-2,6-dinitroaniline (PENDIMETHALIN); methyl 5-(2,4-dichlorophenoxy)-2-nitrobenzoate 2-nitrobenzoate (BIFENOX); N,N-dimethyl-N'-(3-chloro-4-methylphenyl)-urea (CHLORTOLURON); N,N-dimethyl-N'-(4-isopropylphenyl)-urea (ISOPROTURON); methyl 2-[4,5dihydro-4-methyl-4-(1-methylethyl)-5-oxo-1H-imidazol-2-yl]-4 (5)-methylbenzoate (IMAZAMETHABENZ); 3,5-dibromo-4-hydroxybenzonitrile (BROMOXYNIL); 3,5-diiodo-4-hydroxybenzonitrile (IOXYNIL); N-methyl-2-(1,3-benzothiazol-2-yloxy)-acetanilide (MEFENACET); 2-chloro-N-{[(4-methoxy-6-methyl-1,3,5-triazin-2-yl)-amino]-carbonyl}-benzenesulphonamide (CHLORSULFURON); 2-{[[((4-methoxy-6-methyl-1,3,5-triazin-2-yl)-amino)-carbonyl]amino]-sulphonyl }-benzoic acid or its methyl ester (METSULFURON); methyl 3-[[[[(4-methoxy-6-methyl-1,3,5-triazin-2-yl)-amino]-carbonyl]-amino ]-sulphonyl]thiophene-2-carboxylate (THIAMETURON); N,N-diisopropyl-S-(2,3,3,-trichloroallyl)-thiocarbamate (TRI-ALLATE); 2-chloro-4-ethylamino-6-isopropylamino-1,3,5-triazine (ATRAZINE); 2-chloro-4-ethylamino-6-( 3-cyanopropylamino)-1,3,5-triazine (CYANAZINE); 4-ethylamino-2-t-butylamino-6-methylthio-s-triazine (TERBUTRYNE); 4-amino-6-t-butyl-3-ethylthio-1,2,4-triazin-5(4H)-one (ETHIOZINE); 3-isopropyl-2,1,3-benzothiadiazin-4-one 2,2-dioxide(BENTAZONE); and O-(6-chloro-3-phenyl-pyridazin-4-yl ) S-octyl thiocarbonate (PYRIDATE) are also of possible advantage. Surprisingly, some mixtures also show synergistic actions.

A mixture with other known active compounds, such as fungitides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

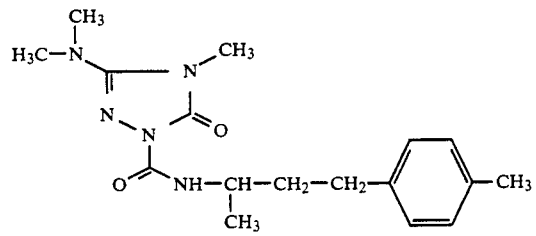

Process a

A solution of 4.08 g (0.025 mol) of 4-(4-methylphenyl)-2-butylamine (compare, for example, DE-OS (German Published Specification ) 3,222,152 ) and 2.53 g (0.025 mol) of triethylamine in 50 ml of acetonitrile is added dropwise with stirring at room temperature to 5.1 g (0.025 mol) of 1-chlorocarbonyl-3-dimethylamino-4-methyl-1,2,4-triazolin-5-one in 100 ml of acetonitrile.

After addition is complete, the mixture is stirred at room temperature for 4 hours, precipitated triethylamine hydrochloride is then filtered off, the filtrate is concentrated in vacuo, the oily residue is taken up in 150 ml of dichloromethane, the solution is washed three times with 50 ml of water in each case and dried over sodium sulphate, and the solvent is removed in vacuo. The residue is chromatographed on silica gel (eluent: cyclohexane/ethyl acetate 1:1).

3.5 g (42% of theory) of 1-[4-(4-methylphenyl)-but-2-ylaminocarbonyl]-3-dimethylamino-4    -methyl-1,2,4-triazolin-5-one are obtained as an oil.

$^1$H-NMR (CDCl$_3$/tetramethylsilane): δ=1.23–1.25; 1.75–1.85; 2.3; 2.6–2.7; 2.85; 3.25; 4.0–4.15; 7.05; 7.85–7.9 ppm.

EXAMPLE 2

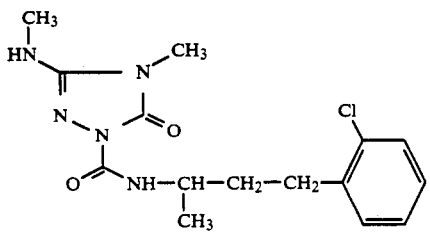

Process a

A solution of 4.58 g (0.025 mol) of 4-(2-chlorophenyl)-2-butylamine (for preparation compare, for example, EP 6,614) and 2.53 g (0.025 mol) of triethylamine in 50 ml of acetonitrile is added dropwise with stirring at room temperature to 4.76 g (0.025 mol) of 1-chloro-carbonyl-3-methylamino-4-methyl-1,2,4-triazolin-5 -one in 100 ml of acetonitrile. After addition is complete, the mixture is stirred at room temperature for 4 hours, precipitated triethylamine hydrochloride is then filtered off and the filtrate is concentrated in vacuo. The solid residue is stirred with water and recrystallised from cyclohexane/ethyl acetate (1:1).

5.8 g (69% of theory) of 1-[4-(2-chlorophenyl)-but-2-ylaminocarbonyl]-3-methylamino-4    -methyl-1,2,4-triazolin-5-one of melting point 133° C. to 135° C. are obtained.

EXAMPLE 3

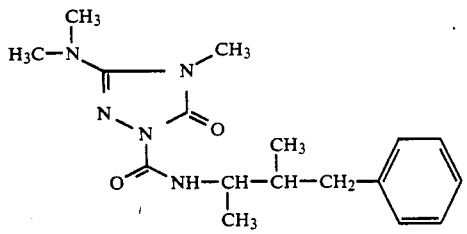

Process b 4.9 g (0.026 mol) of 4-phenyl-3-methyl-but-2-yl isocyanate (for preparation compare, for example, Nouv. J. Chim. 1, 243–254 [1977] and CA 87: 151614a and also DE-OS (German Published Specification) 3,222,152) and 3 drops of 1,8-diazabicyclo-[5.4.0]-undec-7-ene (DBU) are added at room temperature to 3.55 g (0.025 mol) of 3-dimethylamino-4-methyl-1,2,4-triazolin-5-one in 80 ml of acetonitrile, the mixture is stirred at room temperature for 6 hours and concentrated in vacuo, and the residue is chromatographed on silica gel (eluent: cyclohexane/ethyl acetate 1:1).

5.4 g (65% of theory) of 1-(4-phenyl-3-methyl-but-2-ylaminocarbonyl)-3-dimethylamino-4    -methyl-1,2,4-triazolin-5-one are obtained as an oil.

$^1$H-NMR (CDCl$_3$/tetramethylsilane): δ=0.85–0.95; 1.23–1.25; 1.9–2.0; 2.3–2.4; 2.85; 3.25; 4.1–4.2; 7.15–7.25; 8.0–8.1 ppm.

EXAMPLE 4

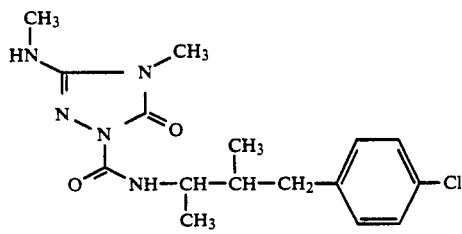

Process b 4.5 g (0.02 mol) of 4-(4-chlorophenyl)-3-methyl-but-2-yl isocyanate ( for preparation compare, for example, Nouv. J. Chim. 1, 243–254 [1977] and CA 87:151614a and also DE-OS (German Published Specification) 3,222,152) and 3 drops of 1,8-diazabicyclo-[5.4.0]-undec-7-ene (DBU) are added at room temperature to 2.56 g (0.02 mol) of 3-methylamino-4-methyl-1,2,4-triazolin-5-one in 80 ml of acetonitrile, the mixture is stirred at reflux temperature for 2 hours and concentrated in vacuo, and the residue is chromatographed on silica gel (eluent: cyclohexane/ethanol 1:1).

3.4 g (48% of theory) of 1-[4-(4-chlorophenyl )-3-methyl-but-2-ylaminocarbonyl]-3    -methylamino-4-methyl-1,2,4-triazolin-5-one of melting point 222° to 224° C. are obtained.

The substituted triazolinones of the general formula (I):

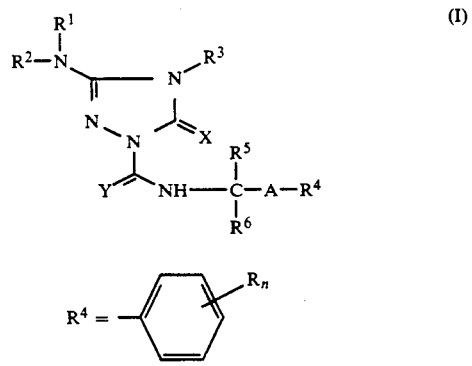

listed in the following table*) are obtained in a corresponding manner and according to the general instructions for preparation.

The $^1$H-NMR spectra were recorded in deuterochloroform (CDCl$_3$) using tetramethylsilane (TMS) as internal standard. The chemical shift is given as the δ value in ppm.

---

$^1$H-NMR*)

-continued

| Ex. No. | $-N(R^1R^2)$ | $R^3$ | $R_n$ | $R^5$ | $R^6$ | A | X | Y | or m.p. [°C.] |
|---|---|---|---|---|---|---|---|---|---|
| 5 | $-N(CH_3)_2$ | $CH_3$ | 4-t-$C_4H_9$ | H | H | $-CH(CH_3)-CH_2-$ | O | O | 0.9–0.95; 1.3; 2.85; 3.25 |
| 6 | $-N(CH_3)_2$ | $CH_3$ | H | $CH_3$ | $CH_3$ | $-CH_2-CH_2-$ | O | O | 1.45; 2.0–2.1; 2.6–2.7; 2.85; 3.25; 7.1–7.3 |
| 7 | $-N(CH_3)_2$ | $CH_3$ | 4-Cl | H | $CH_3$ | $-CH(CH_3)-CH_2-$ | O | O | 1.2–1.25; 3.25; 7.1–7.25 |
| 8 | $-N(CH_3)_2$ | $CH_3$ | 4-Cl | H | H | $-CH(CH_3)-CH_2-$ | O | O | 0.9–0.95; 2.85; 7.1–7.25 |
| 9 | $-N(CH_3)_2$ | $CH_3$ | 4-Cl | H | $CH_3$ | $-CH(C_2H_5)-CH_2-$ | O | O | 2.85; 3.25; 4.05–4.15; 7.1–7.25 |
| 10 | $-N(CH_3)_2$ | $CH_3$ | 4-F | H | $CH_3$ | $-CH(CH_3)-CH_2-$ | O | O | 1.2–1.25; 2.85; 6.9–7.15 |
| 11 | $-N(CH_3)_2$ | $CH_3$ | 2,4-di-Cl | $CH_3$ | $CH_3$ | $-CH_2-CH_2-$ | O | O | 1.45; 2.0–2.1; 2.7–2.8; 2.85 |
| 12 | $-N(CH_3)_2$ | i-$C_3H_7$ | 4-Cl | H | $CH_3$ | $-CH(CH_3)-CH_2-$ | O | O | 1.5–1.55; 2.85; 4.1–4.2; 7.1–7.25; 8.05–8.1 |
| 13 | $-N(CH_3)_2$ | $CH_3$ | H | $CH_3$ | $C_2H_5$ | $-CH_2-CH_2-$ | O | O | 0.9–0.95; 2.6–2.65; 2.85; 7.9 |
| 14 | $-N(CH_3)_2$ | $CH_3$ | H | $C_2H_5$ | $C_2H_5$ | $-CH_2-CH_2-$ | O | O | m.p.: 94–95° C. |
| 15 | $-N(CH_3)_2$ | $CH_3$ | 4-F | $CH_3$ | $CH_3$ | $-CH_2-CH_2-$ | O | O | m.p.: 95–96° C. |
| 16 | $-N(CH_3)_2$ | $CH_3$ | 4-$CH_3$ | $CH_3$ | $CH_3$ | $-CH_2-CH_2-$ | O | O | m.p.: 98° C. |
| 17 | $-N(CH_3)_2$ | $CH_3$ | 3-Cl | $CH_3$ | $CH_3$ | $-CH_2-CH_2-$ | O | O | 1.45; 2.05–2.1; 2.85; 3.25; 4.0–4.1 |
| 18 | $-N(CH_3)_2$ | $CH_3$ | 4-Cl | $CH_3$ | $CH_3$ | $-CH_2-CH_2-$ | O | O | m.p.: 81° C. |
| 19 | $-N(CH_3)_2$ | $CH_3$ | 4-Cl | H | $CH_3$ | $-CH_2-CH_2-$ | O | O | 1.25; 2.6–2.7; 2.85; 3.25; 4.0–4.1 |
| 20 | $-N(CH_3)_2$ | $CH_3$ | 3,4-di-$CH_3$ | H | $CH_3$ | $-CH_2-CH_2-$ | O | O | 1.25; 2.85; 3.25; 4.0–4.1; 7.0–7.1; 7.3–7.35 |
| 21 | $-N(CH_3)_2$ | $CH_3$ | 2-Cl | H | $CH_3$ | $-CH_2-CH_2-$ | O | O | 1.25–1.3; 1.3–1.4; 2.85; 3.25 |
| 22 | $-N(CH_3)_2$ | $CH_3$ | 4-$CH_3$ | H | $CH_3$ | $-C(CH_3)_2-CH_2-$ | O | O | 2.3; 2.85; 3.25; 7.0–7.1 |
| 23 | $-N(CH_3)_2$ | $CH_3$ | 4-$OCH_3$ | H | $CH_3$ | $-CH_2-CH_2-$ | O | O | 1.25; 1.75–1.85; 2.85; 3.75 |
| 24 | $-N(CH_3)_2$ | $CH_3$ | 4-t-$C_4H_9$ | H | $CH_3$ | $-CH_2-CH_2-$ | O | O | 1.3; 2.6–2.7; 2.85; 4.0–4.1 |
| 25 | $-N(CH_3)_2$ | $CH_3$ | 2-Cl | H | $CH_3$ | $-CH(CH_3)-CH_2-$ | O | O | 1.2–1.25; 2.85; 3.25; 7.0–7.25 |
| 26 | $-N(CH_3)_2$ | $CH_3$ | 4-F | H | $CH_3$ | $-CH_2-CH_2-$ | O | O | 1.25; 1.8–1.9; 2.6–2.7; 3.25 |
| 27 | $-N(CH_3)_2$ | $CH_3$ | 3-$CH_3$ | H | $CH_3$ | $-CH(CH_3)-CH_2-$ | O | O | 2.3; 2.85; 3.25; 8.0–8.1 |
| 28 | $-N(CH_3)_2$ | $CH_3$ | 2-$CH_3$ | H | $CH_3$ | $-CH(CH_3)-CH_2-$ | O | O | 2.85; 3.25; 7.05–7.15; 8.0–8.1 |
| 29 | $-N(CH_3)_2$ | $CH_3$ | 3-$CF_3$ | H | $CH_3$ | $-CH_2-CH_2$ | O | O | 1.4; 1.85–1.9; 2.85; 4.05–4.15 |

-continued

| | | | | | | | | | |
|---|---|---|---|---|---|---|---|---|---|
| 30 | —N(CH$_3$)$_2$ | CH$_3$ | 3-OCH$_3$ | H | CH$_3$ | —CH—CH$_2$—<br>$\|$<br>CH$_3$ | O | O | 2.85; 3.25; 3.8; 4.1–4.15; 8.0–8.05 |
| 31 | —N(CH$_3$)$_2$ | CH$_3$ | 3-OC$_2$H$_5$ | H | CH$_3$ | —CH—CH$_2$—<br>$\|$<br>CH$_3$ | O | O | 2.85; 3.25; 3.95–4.05; 8.0–8.1 |
| 32 | —N(CH$_3$)$_2$ | CH$_3$ | 3-O-n-C$_3$H$_7$ | H | CH$_3$ | —CH—CH$_2$—<br>$\|$<br>CH$_3$ | O | O | 2.85; 3.25; 3.85–3.95; 8.0–8.1 |
| 33 | —N(CH$_3$)$_2$ | CH$_3$ | 2-NH—CO—CH$_3$ | H | CH$_3$ | —CH$_2$—CH$_2$— | O | O | 2.15; 2.85; 4.0–4.1; 7.55 |
| 34 | —N(CH$_3$)$_2$ | CH$_3$ | 3,4-di-CH$_3$ | H | CH$_3$ | —CH—CH$_2$—<br>$\|$<br>CH$_3$ | O | O | 2.2; 2.85; 6.9–7.05; 8.0–8.05 |
| 35 | —N(CH$_3$)$_2$ | CH$_3$ | 3-CF$_3$ | H | CH$_3$ | —CH—CH$_2$—<br>$\|$<br>CH$_3$ | O | O | 1.25; 2.85; 3.3; 7.4–7.45 |
| 36 | —N(CH$_3$)$_2$ | CH$_3$ | 2-OC$_2$H$_5$ | H | CH$_3$ | —CH—CH$_2$—<br>$\|$<br>CH$_3$ | O | O | 1.25–1.3; 2.85; 4.0–4.05 |
| 37 | —N(CH$_3$)$_2$ | CH$_3$ | 4-N(CH$_3$)$_2$ | CH$_3$ | CH$_3$ | —CH$_2$—CH$_2$— | O | O | 1.45; 2.0–2.1; 2.85; 2.9; 3.25 |
| 38 | —NH—CH$_3$ | CH$_3$ | 4-Cl | H | CH$_3$ | —CH$_2$—CH$_2$— | O | O | m.p.: 120–121° C. |
| 39 | —NH—CH$_3$ | CH$_3$ | 3-Cl | H | CH$_3$ | —CH$_2$—CH$_2$— | O | O | m.p.: 114–116° C. |
| 40 | —NH—CH$_3$ | CH$_3$ | 3-OCH$_3$ | H | CH$_3$ | —CH—CH$_2$—<br>$\|$<br>CH$_3$ | O | O | m.p.: 124–126° C. |
| 41 | —NH—CH$_3$ | CH$_3$ | 4-CH$_3$ | H | CH$_3$ | —CH$_2$—CH$_2$— | O | O | m.p.: 134–136° C. |
| 42 | —NH—CH$_3$ | CH$_3$ | 3-CF$_3$ | H | CH$_3$ | —CH$_2$—CH$_2$— | O | O | m.p.: 128–130° C. |
| 43 | —NH—CH$_3$ | CH$_3$ | 4-t-C$_4$H$_9$ | H | CH$_3$ | —CH$_2$—CH$_2$— | O | O | m.p.: 136–138° C. |
| 44 | —NH—CH$_3$ | CH$_3$ | 3,4-di-Cl | H | CH$_3$ | —CH$_2$—CH$_2$— | O | O | m.p.: 95–97° C. |
| 45 | —NH—CH$_3$ | CH$_3$ | 4-OCH$_3$ | H | CH$_3$ | —CH$_2$—CH$_2$— | O | O | m.p.: 112–114° C. |
| 46 | —NH—CH$_3$ | CH$_3$ | 3,4-di—CH$_3$ | H | CH$_3$ | —CH—CH$_2$—<br>$\|$<br>CH$_3$ | O | O | m.p.: 143–144° C. |
| 47 | —NH—CH$_3$ | CH$_3$ | 2-OC$_2$H$_5$ | H | CH$_3$ | —CH—CH$_2$—<br>$\|$<br>CH$_3$ | O | O | m.p.: 119–121° C. |
| 48 | —NH—CH$_3$ | CH$_3$ | 3-OC$_2$H$_5$ | H | CH$_3$ | —CH—CH$_2$—<br>$\|$<br>CH$_3$ | O | O | m.p.: 128–130° C. |
| 49 | —NH—CH$_3$ | CH$_3$ | 3-CF$_3$ | H | CH$_3$ | —CH—CH$_2$—<br>$\|$<br>CH$_3$ | O | O | m.p.: 134–135° C. |
| 50 | —N-iC$_3$H$_7$<br>$\|$<br>CH$_3$ | CH$_3$ | 4-Cl | H | CH$_3$ | —CH$_2$—CH$_2$ | O | O | |
| 51 | —N(CH$_3$)$_2$ | CH$_3$ | 4-OC$_2$H$_5$ | H | CH$_3$ | —CH$_2$—CH$_2$— | O | O | 1.35–1.40; 2.6–2.7; 2.85; 3.95–4.05 |
| 52 | —N(CH$_3$)$_2$ | CH$_3$ | 2-Cl | H | H | —CH—CH$_2$—<br>$\|$<br>CH$_3$ | O | O | 0.95–0.97; 2.85; 4.13–4.17 |
| 53 | —N(CH$_3$)$_2$ | CH$_3$ | 3,4-O—CH$_2$—O— | H | CH$_3$ | —CH$_2$—CH$_2$— | O | O | 1.75–1.85; 2.55–2.65; 2.85; 5.9; 6.6–6.7 |
| 54 | —N(CH$_3$)$_2$ | CH$_3$ | 2,3-CH=CH—CH=CH— | H | CH$_3$ | —CH$_2$—CH$_2$— | O | O | 1.92–2.05; 2.85; 4.15–4.25; 7.35–7.50 |
| 55 | —NH—CH$_3$ | CH$_3$ | 4-OC$_2$H$_5$ | H | CH$_3$ | —CH$_2$—CH$_2$— | O | O | m.p.: 132–133° C. |

-continued

| Ex. No. | −N(R¹R²) | $R^3$ | $R^4$ | $R^5$ | $R^6$ | A | X | Y | ¹H-NMR*) or m.p./°C. |
|---|---|---|---|---|---|---|---|---|---|
| 56 | −N(CH₃)(C₂H₅) | CH₃ | 4-Cl | H | CH₃ | −CH₂−CH₂− | O | O | 1.15-1.22; 1.25-1.27; 1.75-1.85; 2.85; 7.8-7.9 |
| 57 | −N(CH₃)(C₂H₅) | CH₃ | 4-Cl | H | CH₃ | −CH(CH₃)−CH₂− | O | O | 0.9-0.95; 2.85; 7.95-8.05 |
| 58 | −N(CH₃)(C₂H₅) | CH₃ | H | H | CH₃ | −CH(CH₃)−CH₂− | O | O | 2.85; 3.10-3.20; 4.0-4.15; 7.15-7.30; 8.05-8.10 |
| 59 | −N(CH₃)₂ | CH₃ | 4-CF₃-C₆H₄− | H | CH₃ | −CH₂−CH₂− | O | O | 1,25-1,27; 1,75-1,8; 2,85; 4,05-4,15; 7,3-7,35; 7,5-7,55 |
| 60 | −N(CH₃)₂ | CH₃ | 4-i-C₃H₇-C₆H₄− | H | H | −CH(CH₃)−CH₂− | O | O | 0,92-0,95; 1,2-1,25; 2,0-2,1; 2,85; 3,25; 7,05-7,15 |
| 61 | −NH−CH₃ | CH₃ | 4-CF₃-C₆H₄− | H | CH₃ | −CH₂−CH₂− | O | O | 1,25-1,27; 1,8-1,9; 2,7-2,85; 2,95-3,0; 3,15; 4,0-4,1 |
| 62 | −NH−CH₃ | CH₃ | 4-i-C₃H₇-C₆H₄− | H | H | −CH(CH₃)−CH₂− | O | O | 0,9-0,95; 1,2-1,25; 2,90-2,95; 3,15; 4,7-4,75 |
| 63 | −N(CH₃)₂ | CH₃ | 4-O-n-C₄H₉-C₆H₄− | H | CH₃ | −CH(CH₃)−CH₂− | O | O | 0,95-1,0; 1,2-1,25; 1,45-1,55; 2,85; 3,9-3,95 |
| 64 | −N(CH₃)₂ | CH₃ | 4-C₂H₅-C₆H₄− | H | CH₃ | −CH₂−CH₂− | O | O | 1,18-1,23; 1,25-1,27; 1,8-1,9; 2,85; 7,1 |
| 65 | −N(CH₃)₂ | CH₃ | 2,4-Cl₂-C₆H₃− | CH₃ | CH₃ | −CH₂−CH₂− | O | O | 1,5; 2,0-2,1; 2,7-2,8; 2,85; 3,25; 8,0 |
| 66 | −NH−CH₃ | CH₃ | 4-Cl-C₆H₄− | H | H | −CH(CH₃)−CH₂− | O | O | Fp 115-116° C. |
| 67 | −N(CH₃)₂ | CH₃ | C₆H₅− | CH₃ | CN | −CH₂−CH₂− | O | O | Fp 172-174° C. |
| 68 | −N(CH₃)₂ | C₂H₅ | 4-Cl-C₆H₄− | H | CH₃ | −CH₂−CH₂− | O | O | 1,35-1,4; 1,8-1,9; 2,88; 3,68-3,75; 7,1-7,25 |
| 69 | −N(CH₃)₂ | C₂H₅ | 4-Cl-C₆H₄− | H | CH₃ | −CH(CH₃)−CH₂− | O | O | 1,3-1,33; 2,85; 3,7-3,8; 8,0-8,05 |

-continued

| | | | | | | | | | |
|---|---|---|---|---|---|---|---|---|---|
| 70 | —N(CH₃)₂ | C₂H₅ | 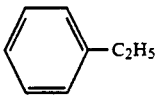 | H | CH₃ | —CH₂—CH₂— | O | O | 1,2–1,38; 1,8–1,9; 2,88; 3,7–3,78; 7,1; 7,87–8,93 |
| 71 | —N(CH₃)₂ | C₂H₅ | 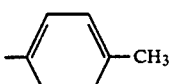 | H | CH₃ | —CH₂—CH₂— | O | O | 1,24–1,27; 2,3; 2,85; 3,7–3,78; 7,1; 7,9–7,95 |
| 72 | —N(CH₃)₂ | C₂H₅ | 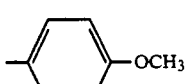 | H | CH₃ | —CH₂—CH₂— | O | O | 1,25–1,28; 2,6–2,7; 2,85; 3,75; 7,85–7,93 |
| 73 | —N(CH₃)₂ | C₂H₅ | 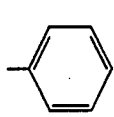 | CH₃ | CN | —CH₂—CH₂— | O | O | Fp 166–168° C. |
| 74 | —N(CH₃)₂ | CH₃ | 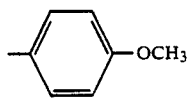 | CH₃ | CN | —CH₂—CH₂— | O | O | Fp 110–111° C. |
| 75 | —N(CH₃)₂ | CH₃ | 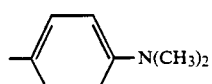 | H | CH₃ | —CH₂—CH₂— | O | O | 1,2–1,45; 2,55–2,7; 2,85; 2,9; 7,85–7,9 |
| 76 | —N(CH₃)₂ | CH₃ | 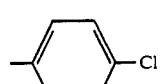 | H | H | —CH₂—C(CH₃)₂— | O | O | Fp 86–88° C. |
| 77 | —N(CH₃)₂ | CH₃ | 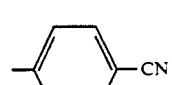 | CH₃ | CH₃ | —CH₂—CH₂— | O | O | Fp 112–113° C. |
| 78 | —N(CH₃)₂ | CH₃ | 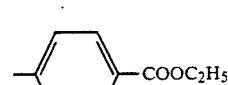 | CH₃ | CH₃ | —CH₂—CH₂— | O | O | Fp 72–74° C. |
| 79 | —N(CH₃)₂ | CH₃ | 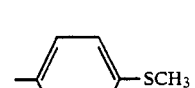 | H | CH₃ | —CH₂—CH₂— | O | O | 1,23–1,26; 2,45; 2,88; 3,27 |
| 80 | —N(CH₃)₂ | CH₃ | 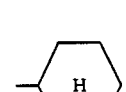 | H | i-C₄H₉ | —CH₂—CH₂— | O | O | 0,9–0,95; 2,85; 3,25; 3,93–4.03 |
| 81 | —N(CH₃)₂ | CH₃ | 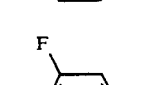 | H | CH₃ | —CH₂—CH₂— | O | O | 1,25–1,28; 1,78–1,88; 2,88; 3,28; 7,85–7,92 |
| 82 | —N(CH₃)₂ | CH₃ | 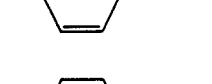 | H | CH₃ | —CH₂—CH₂— | O | O | 0,9–0,95; 1,25–1,28; 1,55–1,65; 2,5–2,55; 2,38; 3,27; 4,0–4,1 |

| | | | | | | | | |
|---|---|---|---|---|---|---|---|---|
| 83 | —N(CH₃)₂ | CH₃ | (2,4-difluorophenyl) | H | CH₃ | —CH₂—CH₂— | O O | 1,25–1,27; 1,8–1,9; 2,6–2,7; 2,88; 3,28 |
| 84 | —N(CH₃)₂ | CH₃ | (cyclohexyl, H) | CH₃ | CH₃ | —CH₂—CH₂— | O O | 1,38; 2,85; 3,25 |

USE EXAMPLES

In the following Use Examples, the compound shown below was employed as a comparison substance:

(A)

[Structure of comparison compound]

1-(4-phenyl-2-butylaminocarbonyl)-3-dimethylamino-4-methyl-1,2,4-triazolin-5-one (disclosed in DE-OS (German Published Specification) 3,709,574).

EXAMPLE A

Pre-emergence Test

Solvent:
  5 parts by weight of acetone
Emulsifier:
  1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison with the development of the untreated control. The figures denote:

0% = no action (like untreated control)
  100% = total destruction

In this test, for example, the compounds according to Preparation Examples 3 and 6 show a clearly superior activity together with comparable crop plant selectivity compared with the prior art.

EXAMPLE B

Post-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison with the development of the untreated control. The figures denote:

0% = no action (like untreated control)
  100% = total destruction

In this test, for example, the compounds according to Preparation Examples 3, 5 and 6 show a clearly superior activity together with comparable crop plant selectivity compared with the prior art.

It will be understood that the specification and examples are illustrative but not limitative of the present invention and that other embodiments within the spirit and scope of the invention will suggest themselves to those skilled in the art.

What is claimed is:

1. A substituted triazolinone of the formula (I)

(I)

[Structure of formula I]

in which
A represents a radical of the formula $-CH_2-CH_2-$; $-CH_2-CH_2-CH_2-$; $-\underset{\underset{CH_3}{|}}{CH}-CH_2-$;

$-\underset{\underset{C_2H_5}{|}}{CH}-CH_2-$; $-\underset{\underset{CH_3}{|}}{\overset{\overset{CH_3}{|}}{C}}-$ or $-\underset{\underset{CH_3}{|}}{\overset{\overset{CH_3}{|}}{C}}-CH_2-$ X represents oxygen or sulphur,
Y represents oxygen or sulphur,
R¹ represents methyl,
R² represents methyl,
R³ represents methyl, $R^4$ represents phenyl which is optionally substituted by $C_{1-4}$-alkyl, $R^5$ represents hydrogen, and $R^6$ represents $C_{4-5}$-alkyl or

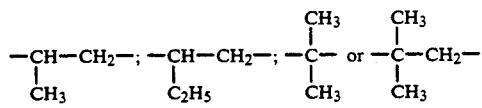

2. The compound 1-(4-phenyl-3-methyl-but-2-ylaminocarbonyl)-3-dimethylamino-4-methyl-1,2,4-triazolin-5-one of the formula

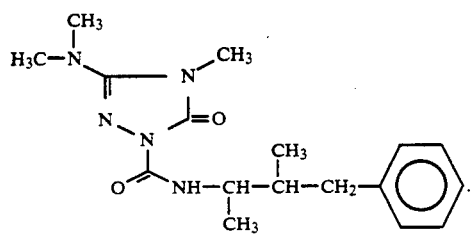

3. The compound 1-(4-phenyl-2-methyl-but-2-ylaminocarbonyl)-3-dimethylamino-4-methyl-1,2,4,-triazolin-5-one of the formula

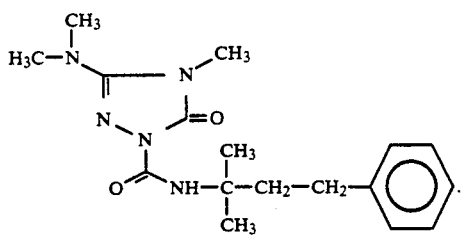

4. The compound 1-(3-(4-tert.-butylphenyl)-2-methylpropylaminocarbonyl)-3-dimethylamino-4-methyl-1,2,4-triazolin-5-one of the formula

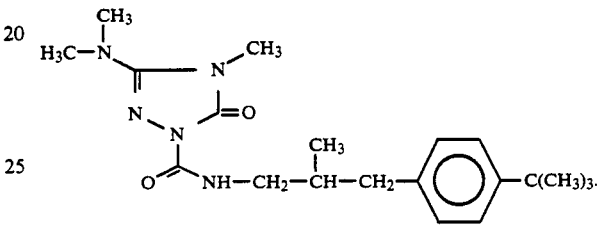

* * * * *

UNITED STATES PATENT AND TRADEMARK OFFICE
CERTIFICATE OF CORRECTION

PATENT NO : 5,332,719
DATED : July 26, 1994
INVENTOR(S): Kurt FINDEISEN, et al.

It is certified that error appears in the above-identified patent and that said Letters Patent is hereby corrected as shown below:

Column 25, line 6, after "alkyl" insert a -- . -- (period) and cancel the balance of the claim Signed and Sealed this Twentieth Day of June, 2000

Attest:

Q. TODD DICKINSON

*Attesting Officer*      *Director of Patents and Trademarks*